(12) United States Patent
Biellak et al.

(10) Patent No.: US 7,463,349 B1
(45) Date of Patent: Dec. 9, 2008

(54) SYSTEMS AND METHODS FOR DETERMINING A CHARACTERISTIC OF A SPECIMEN

(75) Inventors: Stephen Biellak, Sunnyvale, CA (US); David Shortt, Milpitas, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 195 days.

(21) Appl. No.: 11/421,929

(22) Filed: Jun. 2, 2006

(51) Int. Cl.
*G01N 21/00* (2006.01)

(52) U.S. Cl. .................... 356/237.2; 356/237.5

(58) Field of Classification Search ... 356/237.1–237.5, 356/239.1, 239.3, 239.7, 239.8
See application file for complete search history.

(56) References Cited

U.S. PATENT DOCUMENTS

| | | | |
|---|---|---|---|
| 5,274,434 A * | 12/1993 | Morioka et al. | 356/237.4 |
| 5,798,829 A | 8/1998 | Vaez-Iravani | |
| 6,201,601 B1 * | 3/2001 | Vaez-Iravani et al. | 356/237.4 |
| 6,538,730 B2 * | 3/2003 | Vaez-Iravani et al. | 356/237.2 |
| 6,791,680 B1 * | 9/2004 | Rosengaus et al. | 356/237.2 |
| 2004/0042001 A1 | 3/2004 | Vaez-Iravani et al. | |
| 2006/0197946 A1 | 9/2006 | Biellak et al. | |

OTHER PUBLICATIONS

U.S. Appl. No. 60/772,418 entitled Methods and Systems for Determining a Characteristic of a Wafer, filed Feb. 9, 2006.
U.S. Appl. No. 11/110,383 entitled Systems and Methods for Inspecting Specimens Including Specimens That Have a Substantially Rough Uppermost Layer, filed Apr. 20, 2005.

* cited by examiner

*Primary Examiner*—Hoa Q Pham
(74) *Attorney, Agent, or Firm*—Baker & McKenzie LLP (57) ABSTRACT

Systems and methods for determining a characteristic of a specimen are provided. One system includes an illumination subsystem configured to direct light to a first set of spots on the specimen at a normal angle of incidence and to simultaneously direct light to a second set of spots on the specimen at an oblique angle of incidence. The system also includes a detection subsystem configured to detect light scattered from the first and second sets of spots simultaneously and to generate first output responsive to the light scattered from the first set of spots and second output responsive to the light scattered from the second set of spots. The first and second outputs can be used to determine the characteristic of the specimen.

22 Claims, 4 Drawing Sheets

SYSTEMS AND METHODS FOR DETERMINING A CHARACTERISTIC OF A SPECIMEN

BACKGROUND OF THE INVENTION

1. Field of the Invention

This invention generally relates to systems and methods for determining a characteristic of a specimen. Certain embodiments relate to a system configured to direct light to a first set of spots on a specimen at a normal angle of incidence and to simultaneously direct light to a second set of spots on the specimen at an oblique angle of incidence and to detect light scattered from the first and second sets of spots simultaneously.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the device to fail. For instance, as the dimensions of semiconductor devices decrease, detection of defects of decreasing size has become necessary since even relatively small defects may cause unwanted aberrations in the semiconductor devices. Accordingly, much work has been done in the field of wafer inspection to increase the sensitivity of inspection systems to smaller and smaller defects.

In unpatterned or monitor wafer inspection, it is known that, on average, smaller defects can be detected at higher throughput by using light incident on the wafer at an oblique angle from the surface normal, as compared to normal illumination. However, normal incidence illumination has advantages over oblique incidence illumination in other respects. For instance, normal incidence illumination can yield uniform, and sometimes better, detection of scratches, micro-scratches, slip-lines, planar features, and other asymmetric defects of interest.

One way to obtain maximum information from a single wafer inspection includes illuminating the wafer simultaneously at both normal and oblique angles of incidence and collecting surface scatter information from both modalities at once. In addition to simultaneous illumination and collection, the defect detection, processing, and classification subsystems must be able to separate or combine scattered light signals as a function of illumination angle. In this manner, the information obtained using normal incidence illumination and oblique incidence illumination must be separately preserved. Typically, however, using unpatterned surface inspection systems, sequential scans with obliquely incident light and normally incident light are performed to obtain the best capture and classification of surface anomalies and defects. While convenient, this approach does not maximize speed of inspection.

Another advocated approach is to use two inspection wavelengths simultaneously; one wavelength obliquely incident on the wafer, and the second wavelength normally incident on the wafer. In this way, the light collection subsystem may use a physical apparatus, for instance, thin-film filters, to separate the light scattered as a function of incidence angle into separate detectors. Then, two or more detection signals can be generated and sent to the processing subsystem. This approach offers higher throughput than the sequential scan approach, but suffers from the increased cost of additional optical hardware, as well as using two different wavelengths for the inspection. Occasionally, defects or anomalies may have relatively large dispersion (e.g., their scattering properties may depend dramatically on the illuminating wavelength). In these cases, using multiple wavelengths for inspection can be beneficial, and one can argue in favor of dual wavelength detection and classification. But in other cases, a single wavelength is preferred. For instance, the defect detection threshold of the longer of the two wavelengths selected for inspection may be larger in terms of size than that of the shorter wavelength, and the longer wavelength inspection could miss defects.

A third approach is to use the same wavelength simultaneously for illumination at both normal and oblique angles of incidence and to separate inspection at the normal and oblique angles of incidence in either the time domain or in the spatial domain. Time domain separation demands challenging high speed synchrony of the illumination, collection, and data processing subsystems. On the other hand, spatial separation demands that the scattered light collection subsystem direct light scattered from the normally incident illumination to one or more detectors and the light scattered from the obliquely incident illumination to one or more detectors. Currently available inspection systems such as the SP1 and SP2 tools, which are commercially available from KLA-Tencor, San Jose, Calif., have a non-imaging scattered light collector (e.g., a section of an ellipsoidal mirror), and this collector does not permit such spatial separation.

Accordingly, it would be advantageous to develop systems and methods for determining a characteristic of a specimen such as a presence of defects on the specimen that can detect relatively small defects and a relatively large variety of defects with relatively high throughput by illuminating the specimen with one or more wavelengths of light at both normal and oblique angles of incidence and detecting light scattered from the specimen as a function of illumination angle without substantially increasing the complexity or cost of the systems and methods.

SUMMARY OF THE INVENTION

The following description of various system and method embodiments is not to be construed in any way as limiting the subject matter of the appended claims.

One embodiment relates to a system configured to determine a characteristic of a specimen. The system includes an illumination subsystem configured to direct light to a first set of spots on the specimen at a normal angle of incidence and to simultaneously direct light to a second set of spots on the specimen at an oblique angle of incidence. The system also includes a detection subsystem configured to detect light scattered from the first and second sets of spots simultaneously and to generate first output responsive to the light scattered from the first set of spots and second output responsive to the light scattered from the second set of spots. The first and second outputs can be used to determine the characteristic of the specimen.

The first output preferably includes different outputs, each of which is responsive to the light scattered from a different spot of the first set. In addition, the second output preferably includes different outputs, each of which is responsive to the light scattered from a different spot of the second set. If the characteristic of the specimen includes a presence of defects on the specimen, each of the different outputs of the first and second outputs is preferably used to detect the defects on the specimen.

In one such embodiment, the detection subsystem includes a first detection subsystem and a second detection subsystem. The first and second detection subsystems may each include multiple detectors. The first output may include output from each detector of the first detection subsystem, and each detector of the first detection subsystem may be configured to detect light scattered from a different spot of the first set. The second output may include output from each detector of the second detection subsystem, and each detector of the second detection subsystem may be configured to detect light scattered from a different spot of the second set. In this manner, if the characteristic of the specimen includes a presence of defects on the specimen, since each spot of the first and second sets may potentially illuminate a defect that none of the other spots illuminates, the output from each detector of the first and second detection subsystems may be used (e.g., monitored) to detect defects on the specimen.

In one embodiment, the detection subsystem includes a collector objective configured to collect the light scattered from the first and second sets of spots. In another embodiment, the detection subsystem includes a detector configured to detect the light scattered from the first and second sets of spots. In a different embodiment, the detection subsystem includes a first detector configured to detect the light scattered from the first set of spots and a second detector configured to detect the light scattered from the second set of spots. In some embodiments, the detection subsystem is configured to detect the light scattered from the first and second sets of spots in one or more polar collection zones. In one such embodiment, the one or more polar collection zones are selected independently.

In one embodiment, the light directed to the first set of spots and the light directed to the second set of spots has substantially the same wavelength. In another embodiment, the first and second sets of spots are arranged in two different rows of spots on the specimen. In one such embodiment, the two different rows are substantially parallel to each other. In an additional embodiment, the first and second sets of spots are spaced from each other on the specimen. In a further embodiment, the first and second sets of spots are spaced from each other on the specimen to reduce cross talk between the first and second outputs.

In one embodiment, the illumination subsystem is configured such that the first and second sets of spots are directed to substantially the same area of the specimen per unit time. In another embodiment, the illumination subsystem is configured such that the light can be directed to the first set of spots, the second set of spots, or the first and second sets of spots based on the characteristic of the specimen to be determined.

In some embodiments, the first and second sets of spots include the same number of spots. In other embodiments, the first and second sets of spots include different numbers of spots. In a further embodiment, the second set of spots includes a larger number of spots than the first set.

In one embodiment, the spots of the first and second sets have substantially the same aspect ratio. In a different embodiment, the spots of the first and second sets have different aspect ratios. In some embodiments, dimensions and aspect ratios of the spots of the first and second sets are selected based on the characteristic of the specimen to be determined. In another embodiment, an intensity of the spots of the first set is substantially equal to an intensity of the spots of the second set. In a different embodiment, an intensity of the spots of the first set is different than an intensity of the spots of the second set. Each of the embodiments of the system described above may be further configured as described herein.

Another embodiment relates to a method for determining a characteristic of a specimen. The method includes directing light to a first set of spots on the specimen at a normal angle of incidence while simultaneously directing light to a second set of spots on the specimen at an oblique angle of incidence. The method also includes detecting light scattered from the first and second sets of spots simultaneously to generate first output responsive to the light scattered from the first set of spots and second output responsive to the light scattered from the second set of spots. The first and second outputs can be used to determine the characteristic of the specimen.

In one such embodiment, generating the first output includes generating outputs, each of which corresponds to the light scattered from a different spot of the first set. In addition, generating the second output may include generating outputs, each of which corresponds to the light scattered from a different spot of the second set. In this manner, if the characteristic of the specimen includes a presence of defects on the specimen, since each spot of the first and second sets may potentially illuminate a defect that none of the other spots illuminates, the outputs corresponding to each of the different spots of the first and second sets may be used (e.g., monitored) to detect defects on the specimen. Each of the embodiments of the method described above may include any other step(s) described herein.

An additional embodiment relates to another system configured to determine a characteristic of a specimen. The system includes an illumination subsystem configured to direct light to at least one spot on the specimen at a normal angle of incidence and to simultaneously direct light to a set of spots on the specimen at an oblique angle of incidence. The system also includes a detection subsystem configured to detect light scattered from the at least one spot and the set of spots simultaneously and to generate first output responsive to the light scattered from the at least one spot and second output responsive to the light scattered from the set of spots. The first and second outputs can be used to determine the characteristic of the specimen.

The first output preferably includes at least one output, each of which is responsive to the light scattered from a different spot of the at least one spot. In addition, the second output preferably includes different outputs, each of which is responsive to the light scattered from a different spot of the set. If the characteristic of the specimen includes a presence of defects on the specimen, each of the different outputs of the first and second outputs is preferably used to detect the defects on the specimen.

In one such embodiment, the detection subsystem includes a first detection subsystem and a second detection subsystem. The first and second detection subsystems may each include multiple detectors. The first output may include output from each detector of the first detection subsystem, and each detector of the first detection subsystem may be configured to detect light scattered from a different spot of the at least one spot. The second output may include output from each detector of the second detection subsystem, and each detector of the second detection subsystem may be configured to detect light scattered from a different spot of the set. In this manner, if the characteristic of the specimen includes a presence of defects on the specimen, since each spot may potentially illuminate a defect that none of the other spots illuminates, the output from each detector of the first and second detection subsystems may be used (e.g., monitored) to detect defects on the specimen. Each of the system embodiments described above may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "characteristic of a specimen" is used to generally refer to a presence of defects on the specimen, a surface condition of the specimen, a process variation of the specimen, or any other suitable characteristic of interest for the specimen. In addition, as used herein, the term "defect" generally refers to any abnormality or undesirable feature that may be formed on or within a specimen.

As used herein, the term "specimen" refers to a reticle or a wafer. The terms "reticle" and "mask" are used interchangeably herein. A reticle generally includes a transparent substrate such as glass, borosilicate glass, and fused silica having opaque regions formed thereon in a pattern. The opaque regions may be replaced by regions etched into the transparent substrate. Many different types of reticles are known in the art, and the term reticle as used herein is intended to encompass all types of reticles.

As used herein, the term "wafer" generally refers to a substrate formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities. A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dice, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
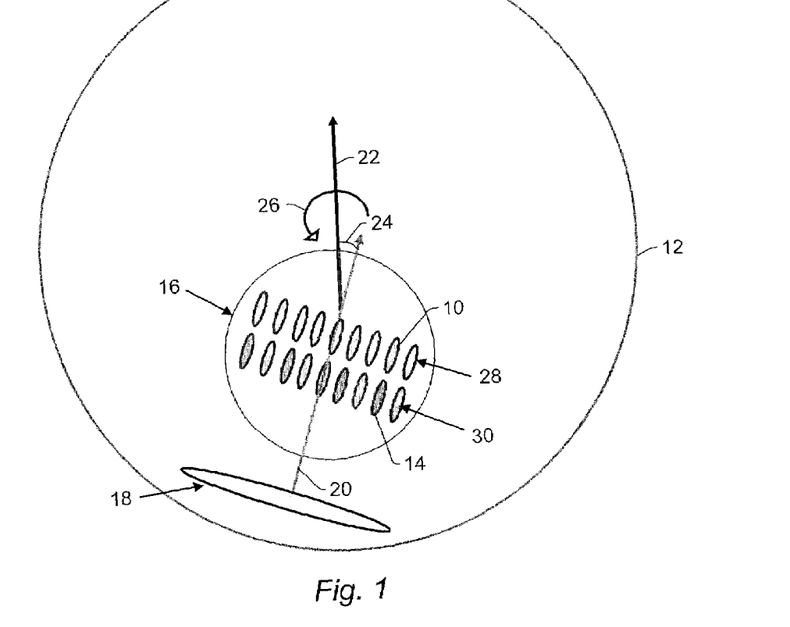
FIG. 1 is a schematic diagram illustrating a top view of a portion of one embodiment of a system configured to determine a characteristic of a specimen.

FIG. 1 illustrates one embodiment of a portion of a system configured to determine a characteristic of a specimen. The system includes an illumination subsystem configured to direct light to a first set of spots 10 on specimen 12 at a normal angle of incidence and to simultaneously direct light to a second set of spots 14 at an oblique angle of incidence. As used herein, the term "a normal angle of incidence" is generally defined as an angle of incidence that is substantially normal to an upper surface of specimen 12. However, "a normal angle of incidence" may not necessarily be exactly normal to the upper surface of the specimen. For example, "a normal angle of incidence" may be defined as an angle of incidence that is within about 1 degree to an exactly normal angle of incidence. The oblique angle of incidence may be any appropriate oblique angle of incidence known in the art.

The first and second sets of spots are shown in FIG. 1 arranged on specimen 12 within field of view 16 of an objective (not shown in FIG. 1). In one embodiment, the illumination subsystem includes this objective through which the light is directed to the first set of spots at a normal angle of incidence. Alternatively, this objective may include a hole (i.e., an opening) through which the light is directed to the first set of spots. Such an embodiment may be advantageous because internal scattering of the normal angle of incidence illumination due to imperfections in the objective would be minimized. The illumination subsystem may also include objective 18 through which the light is directed to the second set of spots at an oblique angle of incidence. The objectives may include any appropriate optical elements known in the art.

Specimen 12 may be disposed upon a stage (not shown) during illumination by the system. As shown in FIG. 1, optical axis 20 of objective 18 is inclined at an angle relative to stage axis 22, also called a linear stage axis or linear axis. As shown in FIG. 1, spots 10 and 14 do not overlap one another, and the spaces between the spots would result in uninspected regions if the scan proceeds with the optical axis parallel to the stage axis (not shown). If, as shown in FIG. 1, optical axis 20 is not parallel to stage axis 22, but instead is offset by offset angle 24 of, for example, about 10 degrees to about 20 degrees, which may vary depending upon the size of spots 10 and 14, the spot separation, and the selected sample spacing in the acquired output, the trajectories of the spots will result in no uninspected regions on the specimen between the spots without overlapping scanned regions within each set of spots. The focal plane of the spots in such an arrangement remains substantially perpendicular to optical axis 20. Circular arrow 26 indicates that the arrangement of spots 10 and 14 may be employed in a spiral scan such as by the specimen rotating with spots 10 and 14 projected thereon by substantially stationary optics.

In the case of a spiral scan, the angular offset between the optical axis and the linear stage axis may be adjusted as a function of rotary stage speed, linear stage speed, spot size, and separation such that the sample spacing of the acquired output has a predetermined size. In the case of a linear scan, the angular offset between the optical axis and the linear stage axis may be adjusted as a function of spot size and spot separation such that the sample spacing of the acquired output has a predetermined size. If the field size of the objective is sufficiently large, the angle between optical axis 20 and stage axis 22 may be relatively small. Such an arrangement may limit the resultant footprint of the system and chance of overlap during data collection. Any tilt of the major and minor axes of each substantially Gaussian spot or spots relative to the spiral tracks may be resolved during post processing of the output.

The system also includes a detection subsystem configured to detect light scattered from the first and second sets of spots simultaneously and to generate first output responsive to the light scattered from the first set of spots and second output responsive to the light scattered from the second set of spots. In this manner, the system shown in FIG. 1 is configured for simultaneous normal and oblique multi-spot illumination and imaging. Preferably, the first output is responsive to the light scattered from the first set of spots but is not responsive to the light scattered from the second set of spots. In addition, the second output is preferably responsive to the light scattered from the second set of spots but not the light scattered from the first set of spots. The first and second outputs can be used to determine a characteristic of the specimen.

The first output preferably includes different outputs, each of which is responsive to the light scattered from a different spot of the first set. In addition, the second output preferably includes different outputs, each of which is responsive to the light scattered from a different spot of the second set. If the characteristic of the specimen includes a presence of defects on the specimen, each of the different outputs of the first and second outputs is preferably used to detect the defects on the specimen.

In one such embodiment, the detection subsystem includes a first detection subsystem and a second detection subsystem. The first and second detection subsystems may each include multiple detectors. The first output may include output from each detector of the first detection subsystem, and each detector of the first detection subsystem may be configured to detect light scattered from a different spot of the first set. The second output may include output from each detector of the second detection subsystem, and each detector of the second detection subsystem may be configured to detect light scattered from a different spot of the second set. In this manner, if the characteristic of the specimen includes a presence of defects on the specimen, since each spot of the first and second sets may potentially illuminate a defect that none of the other spots illuminates, the output from each detector of the first and second detection subsystems may be used (e.g., monitored) to detect defects on the specimen.

In one embodiment, the detection subsystem includes a collector objective (not shown in FIG. 1) configured to collect the light scattered from the first and second sets of spots. For example, in the embodiment shown in FIG. 1, the detection subsystem includes the objective having field of view 16 that is used as a collector objective to collect the light scattered from the first and second sets of spots 10 and 14. In this manner, the light scattered from spots 10 and 14 may be collected by a single collector objective.

In one embodiment, therefore, one objective is used for both normal angle of incidence illumination and collection of light scattered from both normally incident illuminated spots and obliquely incident illuminated spots. In this manner, the first set of spots on the specimen may be illuminated using through-objective illumination. (Alternatively, as described above, the first set of spots on the specimen may be illuminated through a hole in the objective to avoid scattering of the input beam.) In such embodiments, the objective field of view is preferably sufficiently large to image both the light scattered from the first set of spots and the light scattered from the second set of spots (e.g., onto separate arrays of detectors coupled to the collection optics as described further herein).

In one embodiment, the objective may be a relatively large numerical aperture (NA) objective. In one particular example, the objective may have an NA of about 0.9. A first portion of the objective proximate to the optical axis of the objective may be used for directing the light to the first set of spots 10, and a second portion of the objective proximate to and surrounding the first portion of the objective may be used for collecting the light scattered from the first and second sets of spots 10 and 14. In other words, the first portion of the objective may include a relatively small portion of the NA (e.g., about 0.2 NA) proximate to the center of the objective, and the second portion of the objective may include a relatively large portion of the NA (e.g., about 0.7 NA) proximate the edges of the objective.

In one embodiment, as shown in FIG. 1, the first and second sets of spots 10 and 14 are arranged in two different rows 28 and 30, respectively. In this manner, the first and second sets of spots may be arranged in different one-dimensional arrays on the specimen. In addition, the spots in each of the rows may be positioned such that the centers of the spots in each of the rows lie along relatively straight lines (not shown). The spots in each row may be separated from adjacent spots in the row based on a desired sampling level and/or inter-spot cross talk (e.g., cross talk not only between the spots in the different rows, but also between adjacent spots within each row). In one embodiment, the two different rows are substantially parallel to each other, as shown in FIG. 1. For example, a line (not shown) along which the centers of spots 10 are arranged may be substantially parallel to a line (not shown) along which the centers of spots 14 are arranged.

In an additional embodiment, as shown in FIG. 1, the first and second sets of spots are spaced from each other on the specimen. In particular, row 28 is spaced from row 30. In some embodiments, the first and second sets of spots are spaced from each other on the specimen to reduce cross talk between the first and second outputs. In particular, the normally incident spot row is preferably sufficiently separated from the obliquely incident spot row to minimize optical cross talk. In other words, the separation of the rows of spots on the specimen may be selected such that the rows of spots can be considered as completely independent, without producing inter-spot interferences.

In another embodiment, the first set of spots may be arranged in more than one row (not shown) on the specimen. In addition, or alternatively, the second set of spots may be arranged in more than one row (not shown) on the specimen. In this manner, the first and/or second sets of spots may be arranged in different two-dimensional arrays on the specimen. If one or more of the sets of spots are arranged in more than one row on the specimen, each row of spots regardless of which set it belongs to may be spaced from each other row of spots on the specimen as described above.

In a further embodiment, the illumination subsystem is configured such that the first and second sets of spots are directed to substantially the same area of the specimen per unit time. For example, the normally incident spots may be arranged to sample approximately the entire wafer sufficiently with a substantially uniform photon flux (e.g., to capture defects of interest) at substantially the same rate (in $cm^2$ per second) as the obliquely incident spots. In addition, close to the specimen center, the areal scan rates of the normally incident row of spots and the obliquely incident row of spots will begin to differ significantly, but this difference can be accounted for by altering one or more parameters of the system (e.g., spin rate, scan path, stage motion, data acquisition electronics, etc.) while the portion of the specimen relatively close to the specimen center is being illuminated.

As shown in FIG. 1, therefore, a row of normally incident spots has been added to an obliquely incident spot row, such as the obliquely incident spot row described in commonly assigned, co-pending U.S. patent application Ser. Nos. 10/125,906 by Vaez-Iravani et al., which published as U.S. Patent Application Publication No. 2004/0042001, and Ser. No. 11/071,072 by Biellak et al., which are incorporated by reference as if fully set forth herein. As further shown in FIG. 1 and described above, the row of normally incident spots may be substantially parallel to the row of obliquely incident spots and is preferably directed to substantially the same area of the specimen per unit time as the obliquely incident spot row. In this manner, the system embodiments described herein are advantageous over those previously described in that normal incidence scatter information can be obtained simultaneously with oblique incidence scatter information. In particular, the embodiments described herein are configured for simultaneous normal and oblique incidence multi-spot illumination and imaging. In addition, utilizing an illumination configuration employing simultaneous normal and oblique incidence in separate rows of spots as described herein increases the functionality of unpatterned or monitor wafer inspection systems.

Figure 2:
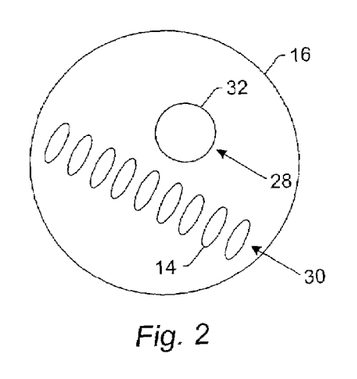
FIGS. 2-3 are schematic diagrams illustrating a top view of various embodiments of a first set of spots and a second set of spots to which light can be directed simultaneously by system embodiments described herein.

In some embodiments, as shown in FIG. 1, the first and second sets of spots include the same number of spots. For example, as shown in FIG. 1, each set of spots includes nine spots. However, the first and second sets of spots may include any other suitable number of spots. In addition, in other embodiments, the first and second sets of spots include different numbers of spots. For example, as shown in FIG. 2, the first set of spots may include only one spot 32, while the second set of spots includes nine spots (spots 14). In one embodiment, therefore, the second set of spots includes a larger number of spots than the first set. In addition, the number of spots included in each set may be selected independently. In another example (not shown), the first set of spots may include a larger number of spots than the second set, and the second set of spots may include only one spot. Furthermore, the sets of spots may include any appropriate number of spots (e.g., one or more normally incident spots and two or more obliquely incident spots).

In another embodiment, the spots of the first and second sets have substantially the same aspect ratio. For example, spots 10 and 14 shown in FIG. 1 have substantially the same aspect ratio. In such embodiments, due to the different angles of illumination, spots 10 and 14 may have different aspect ratios on the specimen unless one of the sets of spots is altered in some manner. For example, due to the illumination angles, spots 10 may have a substantially circular shape on the specimen, and spots 14 may have a generally ellipsoidal shape on the specimen. Therefore, if the aspect ratios of the different sets of spots are selected to be substantially the same, the illumination subsystem may include one or more beam shaping elements (not shown) positioned in the path of the normal incidence illumination or the oblique incidence illumination. In one such example, the one or more beam shaping elements may be configured to alter the shape and/or dimensions of the normal illumination such that the normal incidence spots imaged on the specimen have a generally ellipsoidal shape with an aspect ratio approximately equal to that of the oblique incidence spots. In another such example, the one or more beam shaping elements may be configured to alter the shape and/or dimensions of the oblique illumination such that the oblique incidence spots imaged on the specimen have a generally circular shape with dimensions approximately equal to that of the normal incidence spots.

However, in other embodiments, the spots of the first and second sets have different aspect ratios. For example, as shown in FIG. 2, spot 32 and spots 14 have different aspect ratios. In another embodiment shown in FIG. 3, spots 10 of the first set have different aspect ratios than spots 14 of the second set. In any of the embodiments described herein, dimensions and aspect ratios of the spots of the first and second sets may be selected based on the characteristic of the specimen to be determined (e.g., the defects to be detected on the specimen). In addition, the dimensions and the aspect ratios of the spots of the first and second sets may be selected based on one or more characteristics (e.g., roughness) of the specimen. In particular, spot sizes and spot aspect ratios of normal and oblique incidence illumination may be selected independently to increase, and even maximize, the response to various characteristics of the specimen and/or various defects.

In some embodiments, therefore, the normally incident spot row has the same number of spots and substantially the same spot aspect ratio as the obliquely incident spot row. These equalities are not mandatory, however, as described further above and shown in FIGS. 2 and 3. As described further above, the number of spots and the aspect ratios of the spots may be selected based on the characteristic of the specimen to be determined (e.g., the defects to be detected on the specimen). For example, circular spots may be selected to provide a more uniform scattering response to asymmetrical defects such as scratches. With circular spots, the spot separation and spot diameters may be adjusted with respect to those shown in FIG. 1. In other words, if the aspect ratios of the spots change, the spot separation and dimensions may be altered accordingly (e.g., to prevent overlap of the spots on the specimen). In addition, in the interest of hardware costs, fewer normal incident spots may be employed. For example, even one normally incident spot may be used rather than multiple normally incident spots. In configurations in which one or more characteristics of both sets of the normal incidence spots and the oblique incidence spots are different, the one or more characteristics may be selected such that the different sets of spots are directed to substantially the same area of the specimen per unit time.

Accordingly, another embodiment of a system configured to determine a characteristic of a specimen includes an illumination subsystem configured to direct light to at least one spot on the specimen at a normal angle of incidence and to simultaneously direct light to a set of spots on the specimen at an oblique angle of incidence. The illumination subsystem may be configured as described and shown herein (e.g., as shown in FIGS. 1 and 4-6). The system also includes a detection subsystem configured to detect light scattered from the at least one spot and the set of spots simultaneously and to generate first output responsive to the light scattered from the at least one spot and second output responsive to the light scattered from the set of spots. The detection subsystem may be configured as described and shown herein (e.g., as shown in FIGS. 4-6 and 9-10). The first and second outputs can be used to determine the characteristic of the specimen. The characteristic of the specimen may be determined using the first and second outputs as described further herein.

The first output preferably includes at least one output, each of which is responsive to the light scattered from a different spot of the at least one spot. In addition, the second output preferably includes different outputs, each of which is responsive to the light scattered from a different spot of the set. If the characteristic of the specimen includes a presence of defects on the specimen, each of the different outputs of the first and second outputs is preferably used to detect the defects on the specimen.

In one such embodiment, the detection subsystem includes a first detection subsystem and a second detection subsystem. The first and second detection subsystems may each include multiple detectors. The first output may include output from each detector of the first detection subsystem, and each detector of the first detection subsystem may be configured to detect light scattered from a different spot of the at least one spot. The second output may include output from each detector of the second detection subsystem, and each detector of the second detection subsystem may be configured to detect light scattered from a different spot of the set. In this manner, if the characteristic includes a presence of defects on the specimen, since each spot of the first and second sets may potentially illuminate a defect that none of the other spots illuminates, the output from each detector of the first and second detection subsystems may be used (e.g., monitored) to detect defects on the specimen. Each of the embodiments of the system described above may be further configured as described herein.

In some embodiments, an intensity of spots 10 of the first set is substantially equal to an intensity of spots 14 of the second set. In other embodiments, an intensity of spots 10 of the first set is different than an intensity of spots 14 of the second set. For example, in the interest of sensitivity, depending on the characteristic of the specimen to be determined (e.g., the defects types expected or to be detected on the specimen), the power of the light source (not shown in FIG. 1) such as a laser may be divided equally or unequally between the normal spot row and the oblique spot row as described further herein.

The system shown in FIG. 1 is, therefore, configured for normal and oblique multi-spot illumination and collection. The configuration of the system shown in FIG. 1 is advantageous for a number of reasons. For example, with multi-spot oblique incidence illumination, it is challenging to image more than one spot row on the specimen due to depth of focus considerations. In particular, two rows of equally sized obliquely incident spots generated by one optical system would likely require "best focus" to be placed somewhere between the two rows thereby reducing overall spot quality and depth of focus. Therefore, throughput is fundamentally limited by the objective field of view in addition to other parameters of the system known in the art. On the other hand, the collector objective will likely have an inherently circular field of view, and much of the expense of forming a relatively high NA objective is "wasted" in oblique multi-spot based systems (i.e., much of the field of view "real estate" in the objective is not utilized). Simultaneously utilizing the normally incident spot row and the obliquely incident spot row makes better use of the objective.

A system including the portion of the system shown in FIG. 1 may be further configured as described herein. In addition, the system may be further configured as described in the patent applications by Vaez-Iravani et al. and Biellak et al., which are incorporated by reference above. For example, the system may be further configured as described in these patent applications such that the system has bright field inspection capability, spatial filtering capability (e.g., to block diffraction from patterned features on a specimen), scanning capability, and defect detection capability as described in these patent applications. In addition, the system may include one or more polarizers as described in these patent applications. Furthermore, the system may be configured to perform bright field differential interference contrast mode (utilizing Nomarski's differential interference contrast principles) such as that described in U.S. Pat. No. 5,798,829 by Vaez-Iravani, which is incorporated by reference as if fully set forth herein. The system embodiments described herein may be further configured as described in this patent. In addition, a system that includes the portion of the system shown in FIG. 1 has all of the advantages of other embodiments described herein.

Figure 4:
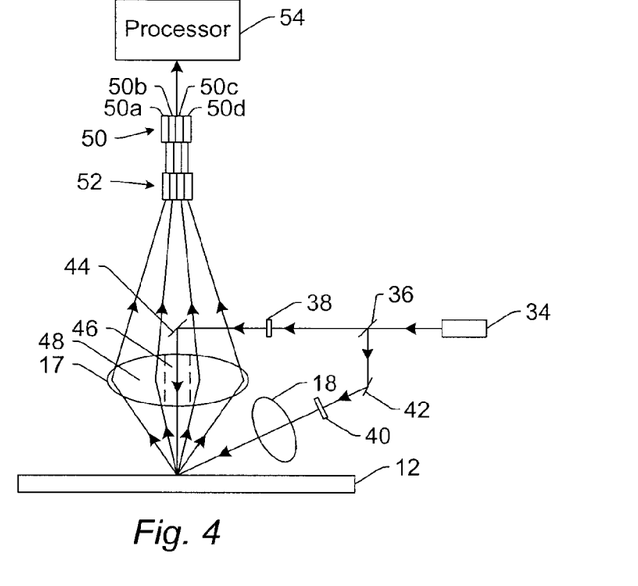
FIGS. 4-6 are schematic diagrams illustrating a side view of various embodiments of a system configured to determine a characteristic of a specimen.

In one embodiment, the light directed to the first set of spots and the light directed to the second set of spots has substantially the same wavelength. One embodiment of a system configured to determine a characteristic of a specimen is shown in FIG. 4, in which the light directed to the first and second sets of spots has substantially the same wavelength. The system shown in FIG. 4 includes an illumination subsystem configured to direct light to the first set of spots (not shown in FIG. 4) on specimen 12 at a normal angle of incidence and to simultaneously direct light to the second set of spots (not shown in FIG. 4) on the specimen at an oblique angle of incidence. For example, as shown in FIG. 4, the illumination subsystem includes light source 34. Light source 34 may be, for example, a laser or any other suitable light source known in the art. In addition, light source 34 may be configured to generate light at any suitable wavelength(s).

Light source 34 may be configured to generate monochromatic light or near monochromatic light. Alternatively, light source 34 may be configured to generate light at multiple wavelengths, and the wavelength that is used may be selected based on, for example, the specimen to be inspected the characteristic to be determined (e.g., the defect(s) to be detected on the specimen). In addition, the illumination subsystem may include one or more optical elements (not shown) such as spectral filters or dichroic mirrors that can be moved into and out of the optical path of the light generated by light source 34 such that the selected wavelength of light can be used.

The illumination subsystem may include beam splitter 36 positioned in the path of the light generated by light source 34. Beam splitter 36 may be, for example, a 50/50 beam splitter. In other words, the beam splitter may split the light from light source 34 into two beams of light having approximately the same intensity. One of the beams of light may be used for oblique incidence illumination, and the other beam of light may be used for normal incidence illumination. In this manner, the intensities of the first and second sets of spots may be approximately the same.

Alternatively, beam splitter 36 may be configured to split the light from light source 34 into two beams of light having different intensities. In this manner, the intensities of the first and second sets of spots may be different. In another alternative, the beam splitter may split the light into two beams of light having approximately the same intensity, and an optical element (not shown) configured to alter the intensity of the light may be inserted into the optical path of one of the two beams of light exiting the beam splitter. For example, the optical element may be a neutral density (ND) filter. In addition, such an optical element may be positioned in the path of both of the beams of light exiting the beam splitter, and each of the optical elements may alter the intensity of the light to the same degree or to different degrees. In this manner, the intensities of the first and second sets of spots on the specimen may be different.

Furthermore, in some instances, it may be advantageous to use different intensities of the first and second sets of spots for determining the characteristic of different specimens. Therefore, in some embodiments, the illumination subsystem may include different beam splitters (not shown) configured to split light in different ratios, and the beam splitter that is positioned in the path of the light generated by light source 34 can be altered depending on the specimen or the characteristic of the specimen to be determined by the system. For example, the system may include a control subsystem (not shown) configured to position one of the beam splitters in the path of the light depending on the characteristic to be determined by the system. In another embodiment, the illumination subsystem may also or alternatively include different optical elements (not shown) that can alter the intensity of a light beam to different degrees. In this manner, the optical element positioned in the path of one or both of the light beams exiting beam splitter 36 may be altered depending on the specimen or the characteristic of the specimen to be determined by the system.

In some embodiments, the illumination subsystem includes diffractive optical elements 38 and 40, each of which is positioned in the path of one of the light beams exiting beam splitter 36. In this manner, different diffractive optical elements may be positioned in the beam of light directed to the specimen at a normal angle of incidence and the beam of light directed to the specimen at an oblique angle of incidence. The characteristics of spots imaged on the specimen depend on the characteristics of the diffractive optical elements. As such, first and second sets of spots having different characteristics such as dimension, aspect ratio, shape, or some combination thereof may be illuminated on the specimen at the same time.

The illumination subsystem may include multiple diffractive optical elements (not shown), each of which may be inserted into the path of a light beam (e.g., the normal incidence light or the oblique incidence light) exiting the beam splitter. Each of the different diffractive optical elements may be configured to diffract the light differently such that a set of spots having different characteristics (e.g., number, dimension, aspect ratio, etc., or some combination thereof) may be generated by each of the diffractive optical elements. In this manner, the diffractive optical element that is positioned in the path of each of the light beams exiting the beam splitter may be altered depending on the specimen to be inspected by the system or the characteristic of the specimen to be determined (e.g., based on the defects to be detected on the specimen). In addition, the diffractive optical element that is positioned in the path of each of the light beams exiting the beam splitter may be altered depending on the wavelength of light used for illumination (e.g., in a wavelength selectable system) since diffraction by diffractive optical elements is wavelength dependent. In another embodiment, the multiple diffractive optical elements may be replaced by a single optical element (not shown) on which multiple diffractive patterns are formed. In this manner, to alter one or more characteristics of the spots on the specimen, the position of the single optical element in the path of one of the light beams may be altered to position a different diffractive pattern in the path of the light.

Although the illumination subsystem is shown to include one diffractive optical element positioned in the path of each of the two beams of light exiting beam splitter 36, it is to be understood that the illumination subsystem may include one diffractive optical element (not shown) positioned in the optical path between light source 34 and beam splitter 36. In such embodiments, the illumination subsystem may include one or more beam shaping optical elements (not shown) positioned in the path(s) of the light transmitted and/or reflected by the beam splitter such that one or more characteristics (e.g., dimension, aspect ratio, etc.) of the first and second sets of spots on the specimen may be different than each other or the same as each other. The one or more beam shaping optical elements may include any suitable beam shaping optical element(s) known in the art.

As shown in FIG. 4, light reflected by beam splitter 36 is directed to diffractive optical element 40 by reflective optical element 42, which may be a folding mirror or any other suitable optical element known in the art. Light exiting diffractive optical element 40 is directed to specimen 12 at an oblique angle of incidence by objective 18, which may be configured as described herein. Diffractive optical element 40 may be positioned at the back focal plane of objective 18 such that the beams of light produced by the diffractive optical element are focused to the surface of specimen 12 as a plurality of beams that are substantially parallel to one another along the optical path. In this manner, objective 18 directs light to the second set of spots on the specimen at an oblique angle of incidence.

As further shown in FIG. 4, light exiting diffractive optical element 38 may be directed to reflective optical element 44, which may be a folding mirror or any other suitable reflective optical element known in the art. Light reflected by reflective optical element 44 is directed to objective 17, which may be configured as described above. Diffractive optical element 38 may be positioned at the back focal plane of objective 17 such that the beams of light produced by the diffractive optical element are focused to the surface of specimen 12 as a plurality of beams that are substantially parallel to one another along the optical path and substantially perpendicular to the surface of the specimen. Objective 17 is configured to direct light to the first set of spots on the specimen at a normal angle of incidence. For example, objective 17 may be a relatively high NA objective. In addition, the light may be directed to specimen 12 at a substantially normal angle of incidence through central portion 46 of objective 17. Central portion 46 may span, for example, the central 0.2 NA of the objective.

In an alternative embodiment, light reflected by reflective optical element 44 may be directed through a hole (not shown) in objective 17. In one such embodiment, light reflected by reflective optical element 44 may be directed through a separate objective (not shown) or a "secondary objective" before passing through the hole in objective 17. This separate objective may direct the light to the first set of spots on the specimen at a normal angle of incidence. The separate objective may include any suitable refractive and/or reflective optical elements known in the art. In such an embodiment, diffractive optical element 38 may be positioned at the back focal plane of the separate objective such that the beams of light produced by the diffractive optical element are focused to the surface of specimen 12 as a plurality of beams that are substantially parallel to one another along the optical path and substantially perpendicular to the surface of the specimen. Furthermore, in such embodiments, reflective optical element 44 may be positioned between objective 17 and specimen 12. For example, reflective optical element 44 may be mounted on the bottom (i.e., wafer side) center of the objective. In this manner, the light directed to the first set of spots on the specimen may not pass through objective 17 or a hole in objective 17.

In an alternative such embodiment, light exiting diffractive optical element 38 may be directed to a separate objective (not shown), and light from the separate objective may be directed to reflective optical element 44. The separate objective may include any suitable refractive and/or reflective optical elements known in the art. In such an embodiment, diffractive optical element 38 may be positioned at the back focal plane of the separate objective such that the beams of light produced by the diffractive optical element are focused to the surface of specimen 12 as a plurality of beams that are substantially parallel to one another along the optical path and substantially perpendicular to the surface of the specimen. In this embodiment, reflective optical element 44 is configured to direct light to the first set of spots on the specimen at a normal angle of incidence. Furthermore, in such embodiments, reflective optical element 44 may be positioned between objective 17 and specimen 12. For example, reflective optical element 44 may be mounted on the bottom (i.e., wafer side) center of the objective. In this manner, the light directed to the first set of spots on the specimen may not pass through objective 17 or a hole in objective 17.

The illumination subsystem of the system shown in FIG. 4 may, therefore, simultaneously direct light of substantially the same wavelength to a first set of spots at a normal angle of incidence and to a second set of spots at an oblique angle of incidence. The first and second sets of spots may be arranged on the specimen according to any of the embodiments described herein.

In some embodiments, the illumination subsystem is configured such that the light can be directed to the first set of spots, the second set of spots, or the first and second sets of spots based on the characteristic of the specimen to be determined (e.g., the defects to be detected on the specimen). For instance, although the illumination subsystem is configured to simultaneously direct light to multiple spots on a specimen at a normal angle of incidence and multiple spots on the specimen at an oblique angle of incidence, the system does not necessarily have to be used in this manner for all specimens. In particular, normal and oblique incidence may be employed, or not employed, for a particular specimen depending on the characteristic of the specimen to be determined (e.g., the defects of interest to be captured on the specimen). In addition, for some specimens, light scattering from the normal incidence illuminated multiple spots or the oblique incidence illuminated multiple spots may provide sufficient information for determining the characteristic of the specimen. In this manner, to reduce the data processing performed for such specimens, light may be directed to only one of the sets of spots.

In such embodiments, the illumination subsystem may include one or more optical elements (not shown) that can be used to control the spots on the specimen to which the light is directed. For instance, the one or more optical elements may include shutters that can be moved (e.g., by a control subsystem (not shown)) into or out of the path of the light beams exiting the beam splitter depending on whether the normal incidence spots and/or the oblique incidence spots are used for illumination of the specimen. In another instance, the control subsystem may be configured to move beam splitter 36 out of the path of the light generated by light source 34 if obliquely incidence spots are not to be used for illumination of a particular specimen. The control subsystem may include any suitable control subsystem known in the art.

The system shown in FIG. 4 also includes a detection subsystem configured to detect light scattered from the first and second sets of spots simultaneously and to generate first output responsive to the light scattered from the first set of spots and second output responsive to the light scattered from the second sets of spots. The first and second outputs can be used to determine the characteristic of the specimen as described further herein.

In one such embodiment, the first output includes different outputs, and each output corresponds to the light scattered from a different spot of the first set. In addition, the second output may include different outputs, and each output corresponds to the light scattered from a different spot of the second set. In this manner, if the characteristic of the specimen includes a presence of defects on the specimen, since each spot of the first and second sets may potentially illuminate a defect that none of the other spots illuminate, each of the different outputs of the first and second outputs may be used (e.g., monitored) to detect defects on the specimen.

The detection subsystem of the system shown in FIG. 4 includes objective 17. Objective 17 may be configured as described above. The detection subsystem, therefore, includes a collector objective configured to collect the light scattered from the first and second sets of spots. In this manner, the detection subsystem may include a single objective configured to collect the light scattered from the first and second sets of spots.

As described further above, objective 17 may be a relatively high NA objective, and the normal illumination may be directed through central portion 46 of the objective. In addition, the light scattered from the first and second sets of spots may be collected through portion 48 of objective 17. Portion 48 may span the outer NA of the objective surrounding the central portion. If the objective has an NA of about 0.90, portion 48 may encompass about 0.7 NA of the objective. Portion 48 may be larger than central portion 46 of objective 17 to enhance sensitivity. Although light scattered from the first and/or second sets of spots may be collected in central portion 46 of the objective, this light may be substantially prevented from reaching the detector(s) of the detection subsystem by reflective optical element 44. One example of an imaging collector that may be utilized as objective 17 is the imaging collector described in the patent applications by Vaez-Iravani et al. and Biellak et al. incorporated by reference above. In particular, the imaging collector described in these patent applications is a multi-element lens that can be used for simultaneous normal and oblique illumination and collection.

Light collected by the objective may be directed to one or more detectors of the detection subsystem. In addition, since the first and second sets of spots are spatially separated from each other on the specimen, light scattered from the first and second sets of spots will be spatially separated, and the objective preferably retains the spatial separation of the light scattered from the first set of spots and the light scattered from the second set of spots. As such, the light scattered from the first set of spots and the light scattered from the second set of spots can be separately detected by the one or more detectors of the detection subsystem. In addition, the light scattered from each spot of the first and second sets can be separately detected by the one or more detectors of the detection subsystem.

In some embodiments, the detection subsystem includes a detector configured to detect the light scattered from the first and second sets of spots. For example, in one embodiment, the detection subsystem includes detector 50. In one such embodiment, the detector may be an array detector that has a plurality of photosensitive elements. For example, the detector may include a charge coupled device (CCD), a time delay integration (TDI) camera, a multi-anode photomultiplier tube (PMT), or any other suitable array detector known in the art. In this manner, different photosensitive elements or different portions of the detector may be used to separately detect the light scattered from the first set of spots and the light scattered from the second set of spots. In addition, different photosensitive elements or different portions of the detector may be used to separately detect the light scattered from each spot of the first and second sets.

In the embodiments described above, the different photosensitive elements or different portions of the detector may be divided into a first detection subsystem and a second detection subsystem of the detection subsystem. The first and second detection subsystems may each include multiple photosensitive elements or multiple portions of the detector. The first output may include output from each photosensitive element or each portion of the first detection subsystem, and the output from each photosensitive element or each portion of the first detection subsystem corresponds to the light scattered from a different spot of the first set. The second output may include output from each photosensitive element or each portion of the second detection subsystem, and the output from each photosensitive element or each portion of the second detection subsystem corresponds to the light scattered from a different spot of the second set. In this manner, if the characteristic of the specimen includes a presence of defects on the specimen, since each spot of the first and second sets may potentially illuminate a defect that none of the other spots illuminates, the output from each photosensitive element or each portion of the first and second detection subsystems may be used (e.g., monitored) to detect defects on the specimen.

In one such embodiment, the detection subsystem includes set of optical fibers or optical light-guides 52. Objective 17 may be configured to image the collected light onto the entrance plane of the set of optical fibers. The set of optical fibers may be configured to separately collect the light scattered from the first set of spots, the light scattered from the second set of spots, and the light scattered from each spot of the first and second sets. In addition, the set of optical fibers may be configured to direct the separately collected portions of the light scattered from the specimen to different portions 50*a*, 50*b*, 50*c*, and 50*d* of detector 50. In this manner, the detection subsystem may simultaneously and separately detect the light scattered from the first set of spots, the light scattered from the second set of spots, and the light scattered from each spot of the first and second sets. Although detector 50 is shown in FIG. 4 to include four different portions, it is to be understood that the detector may include any suitable number of different portions (e.g., two or more different portions). For instance, the detector may include a number of portions equal to the total number of spots illuminated on the specimen at the same time. In this manner, each portion of the detector may detect light scattered from only one corresponding spot on the specimen. The different portions of the detector may be physically separated from each other or may be electronically separated from each other. In addition, the detection subsystem may or may not include the set of optical fibers.

In a different embodiment, the detection subsystem includes a first detector configured to detect the light scattered from the first set of spots and a second detector configured to detect the light scattered from the second set of spots. For example, in the embodiment shown in FIG. 4, different portions 50*a*, 50*b*, 50*c*, and 50*d* of detector 50 may be replaced by separate detectors. Each of the detectors may include a one-dimensional or two-dimensional array detector. Alternatively, the detection subsystem may include a plurality of first detectors and a plurality of second detectors, and each of the first detectors and each of the second detectors may include a PMT or other single photosensitive element detector such as an avalanche photodiode (APD). In such an embodiment, different portions of the light collected by objective 17 may be separately collected by set of optical fibers or optical light-guides 52. In addition, each of the optical fibers of the set may be configured to direct light to a different detector. In this manner, the detection subsystem may simultaneously and separately detect the light scattered from the first set of spots, the light scattered from the second set of spots, and the light scattered from each spot of the first and second sets. Although the detection subsystem is shown in FIG. 4 to include four different detectors, it is to be understood that the detection subsystem may include any suitable number of detectors (e.g., two or more different detectors). For instance, the detection subsystem may include a number of detectors equal to the total number of spots illuminated simultaneously on the specimen. In addition, this embodiment of the detection subsystem may or may not include the set of optical fibers.

In this manner, each detector may detect light scattered from only one corresponding spot on the specimen. In the embodiments described above, the different detectors may be divided into a first detection subsystem and a second detection subsystem of the system. The first and second detection subsystems may each include multiple detectors. In this manner, the first output may include different outputs from each detector of the first detection subsystem, and each detector of the first detection subsystem corresponds to a different spot of the first set. The second output may include different outputs from each detector of the second detection subsystem, and each detector of the second detection subsystem corresponds to a different spot of the second set. In this manner, if the characteristic of the specimen includes a presence of defects on the specimen, since each spot of the first and second sets may potentially illuminate a defect that none of the other spots illuminates, each of the different outputs from each detector of the first and second detection subsystems may be used (e.g., monitored) to detect defects on the specimen.

The system shown in FIG. 4 may include processor 54. Processor 54 is coupled to the detection subsystem of the system. For example, the processor may be coupled to the single detector or the two or more detectors of the detection subsystem by one or more transmission media (not shown). The one or more transmission media may include any suitable transmission media known in the art. Preferably, the processor is coupled to the detection subsystem such that the processor can receive the first and second outputs generated by the detection subsystem.

The processor may be configured to use the first and second outputs to determine the characteristic of the specimen. For example, if the characteristic of the specimen includes a presence of defects on the specimen, since each spot of the first and second sets may potentially illuminate a defect that none of the other spots illuminates, and since the first and second outputs may include different outputs, each corresponding to the light scattered from only one of the spots of the first and second sets, all of the different outputs included in the first and second outputs may be used (e.g., monitored) by the processor to detect defects on the specimen. The processor may be configured to use any suitable method and/or algorithm to detect the defects on the specimen. In addition, the processor may be configured to perform any other defect-related functions known in the art using any suitable method and/or algorithm known in the art. Furthermore, the processor may include any suitable hardware and/or software known in the art.

In another example, the characteristic of the specimen determined by the processor may include a surface condition of the specimen, a process variation of the specimen, or any other suitable characteristic known in the art. In this manner, the embodiments described herein can be used to detect defects such as contaminants and particles and/or one or more other characteristics of the specimen. As such, the system embodiments described herein may be configured as inspection systems that can be used to detect defects on the specimen as in a typical inspection process as well as to determine other characteristic(s) of the specimen that are not typically determined in such an inspection process. The processor may determine such characteristic(s) of the specimen as described in commonly assigned, co-pending U.S. Patent Application Ser. No. 60/772,418 by Kirk et al. filed Feb. 9, 2006, which is incorporated by reference as if fully set forth herein. Processor 54 may be configured to use the first and second outputs described herein to determine a characteristic of the specimen as described in this patent application. In addition, the embodiments described herein may be further configured as described in this patent application.

Obviously, the overall data rate of the system shown in FIG. 4 is substantially greater than a single angle of incidence-based system, with concomitant increased costs in hardware and software. Presumably, this increased cost will be justified by the improved throughput of the system and increased capabilities of the system that the embodiments described herein can offer. Furthermore, if sequential normal and oblique incidence scans were to be considered, and only one set of detection hardware was employed in order to save money, the opto-mechanical alignment tolerance of imaging both normal and oblique incidence illuminated spots on a single fixed detector array could become a limiting factor in system performance. The system embodiment shown in FIG. 4 may be further configured as described herein. In addition, the system shown in FIG. 4 may be further configured as described in the patent applications by Vaez-Iravani et al. and Biellak et al. and the patent to Vaez-Iravani, which are incorporated by reference above. Furthermore, the system shown in FIG. 4 has all of the advantages of other embodiments described herein.

While the single wavelength configuration of the system described above is preferred from a cost perspective, the use of dual- or multi-wavelengths is not precluded from the embodiments described herein. One embodiment of a system configured to determine a characteristic of a specimen using multiple wavelengths is shown in FIG. 4. In this embodiment of the system, the illumination subsystem may include light source 34 as described above. However, unlike the embodiments described above in which light source 34 includes a single wavelength or near monochromatic light source, light source 34 may be, in this embodiment, a multi-wavelength or broadband light source. Light source 34 may include any suitable such light source (e.g., a multi-wavelength laser). In such an embodiment, beam splitter 36 may be configured as a dichroic mirror or other suitable optical element that reflects and transmits light having different wavelengths. For example, light of one wavelength may be transmitted by the beam splitter while light of a different wavelength may be reflected by the beam splitter. In this manner, light having different wavelengths may be directed to the specimen at a normal angle of incidence and an oblique angle of incidence simultaneously.

Figure 5:
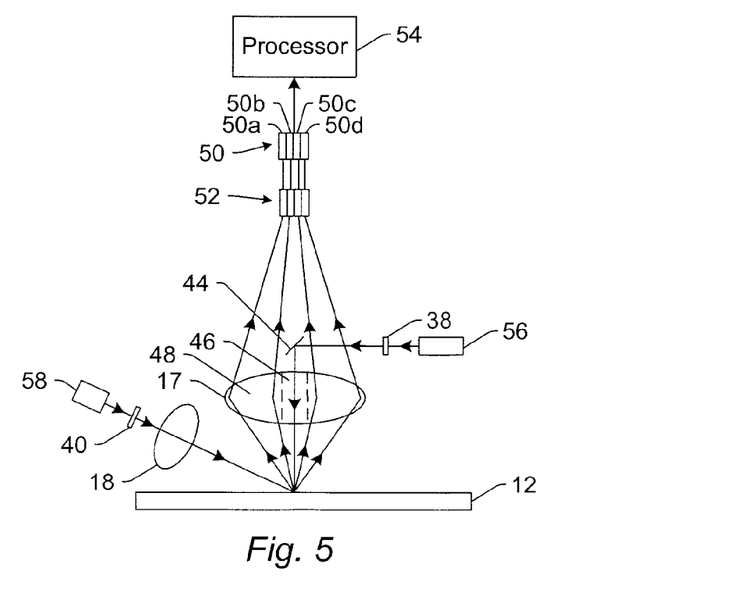

Another embodiment of a system that is configured to determine a characteristic of a specimen using more than one wavelength is illustrated in FIG. 5. Unlike the system shown in FIG. 4, this system embodiment includes two light sources, which may be configured to generate light at different wavelengths. In particular, as shown in FIG. 5, the system may include light sources 56 and 58. Light sources 56 and 58 are, in one embodiment, configured to generate light at different wavelengths. The different wavelengths may include any suitable wavelengths known in the art. Light sources 56 and 58 may include any suitable light sources known in the art. In addition, light sources 56 and 58 may be the same type of light source (e.g., lasers) or different types of light sources (e.g., a laser and a lamp).

As shown in FIG. 5, light from light source 56 is directed to diffractive optical element 38, which may be configured as described above. Light exiting diffractive optical element 38 is directed to objective 17 by reflective optical element 44, both of which may be configured as described herein. In this manner, light generated by light source 56 may be directed to the first set of spots (not shown in FIG. 5) on the specimen at a normal angle of incidence. Alternatively, the system may be configured to direct light from light source 56 to the first set of spots according to any of the other embodiments described herein.

As further shown in FIG. 5, light from light source 58 is directed to diffractive optical element 40, which may be configured as described above. Light exiting diffractive optical element 40 is directed to specimen 12 at an oblique angle of incidence by objective 18, which may be configured as described herein. In this manner, light generated by light source 58 may be directed to the second set of spots (not shown in FIG. 5) on the specimen at an oblique angle of incidence. The system shown in FIG. 5 may be further configured as described herein. In addition, the system shown in FIG. 5 has all of the advantages of other embodiments described herein.

In another embodiment, normal and oblique scatter can be collected in one or more polar collection zones independently. As used herein, the term "polar collection zone" generally refers to a defined range of polar angles over which scattered light is collected from the specimen (e.g., by the objective). In one such embodiment, the detection subsystem is configured to detect the light scattered from the first and second sets of spots in one or more polar collection zones. In one such embodiment, the one or more polar collection zones are selected independently. Each of the polar collection zones may span a set of polar collection angles. For each set of polar collection angles, normal and oblique incident scatter can be collected by two separate rows of detectors (not shown), conveniently physically separated and aligned. The two separate rows of detectors may be configured as described further herein. In addition, or alternatively, normal and oblique scatter can be collected in one or more azimuthal collection zones independently. As used herein, the term "azimuthal collection zone" generally refers to a defined range of azimuthal angles over which scattered light is collected from the specimen (e.g., by the objective).

Figure 6:
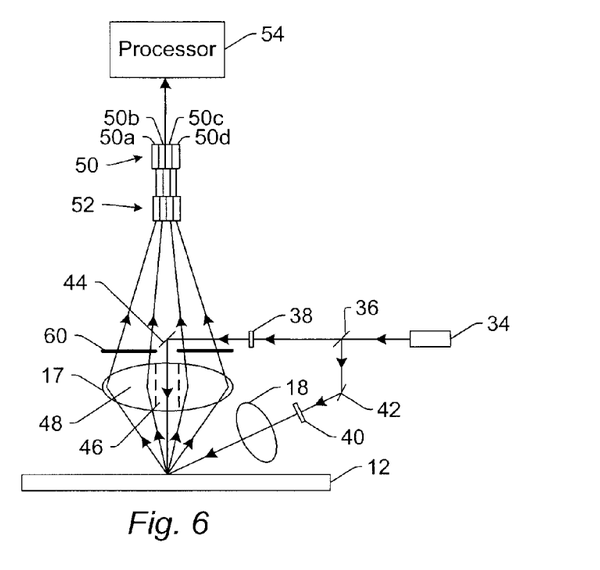

One embodiment of a system configured to determine a characteristic of a specimen by collecting normal and oblique scatter in one or more polar collection zones and/or one or more azimuthal collection zones independently is shown in FIG. 6. In this embodiment, the detection subsystem includes aperture 60. Aperture 60 is configured to alter the polar and/or azimuthal collection zones in which light scattered from the first and second sets of spots is directed to the detector(s) of the detection subsystem. Aperture 60 is positioned in the path of the scattered light that is collected by objective 17. For example, aperture 60 may be placed at the Fourier plane of the objective. In this manner, aperture 60 may be configured to function as a spatial filter. In addition, if aperture 60 is located at the Fourier plane of the optical system, aperture 60 will filter the scattered light from all spots on the specimen equally (e.g., substantially uniformly) as a function of both polar angle and azimuthal angle. In this manner, at the Fourier plane, the scattered light from all spots on the specimen can simultaneously be spatial filtered by selecting various polar and/or azimuthal collection zones to pass or reject. As such, the aperture can be used to block unwanted light from being detected by the detection subsystem. It is noted that although, due to illumination symmetry, spatial filtering the light scattered from the normal incidence illuminated spots in azimuthal angle may not necessarily be useful, but in many cases will not substantially impact sensitivity.

Aperture 60 may be adjustable such that the one or more polar and/or azimuthal collection zones can be selected independently. Furthermore, aperture 60 may be adjustable such that the one or more polar and/or azimuthal collection zones may be altered depending on the specimen or the characteristic of the specimen to be determined (e.g., the defects to be detected on the specimen). For example, aperture 60 may be a programmable liquid crystal spatial filter, and the transmission characteristics of such a spatial filter can be adjusted in any manner known in the art. Aperture 60 may also be adjustable in any other manner known in the art. Furthermore, the detection subsystem may include two or more apertures (not shown). For example, the detection subsystem may include one aperture positioned at the Fourier plane of the system and configured to control the one or more azimuthal collection zones in which the scattered light is detected and another aperture that may be positioned downstream of the first aperture and that is configured to control the one or more polar collection zones in which the scattered light is detected. Moreover, the aperture(s) described herein may be replaced with any other suitable spatial filter(s) known in the art. The system shown in FIG. 6 may be further configured as described herein and has all of the advantages of other embodiments described herein.

Figure 7:
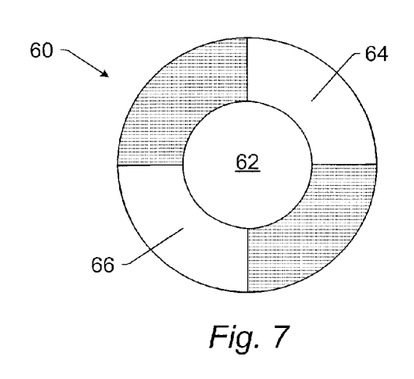
FIGS. 7-8 are schematic diagrams illustrating a top view of various embodiments of an aperture configured such that light can be detected in two or more azimuthal collection zones and/or two or more polar collection zones.

One embodiment of aperture 60 is shown in FIG. 7. As shown in FIG. 7, aperture 60 may include central opening 62 configured such that light from reflective optical element 44 shown in FIG. 6 can pass through the central opening. However, if the aperture is positioned in the system above reflective optical element 44, the aperture may not include central opening 62 shown in FIG. 7. Instead, the central portion of the aperture may be configured to block light. Aperture 60 also includes openings 64 and 66. Openings 64 and 66 are configured to allow light scattered from the first and second sets of spots in one or more azimuthal collection zones to pass through the openings. In this manner, when viewed at the plane of aperture 60, the azimuthal collection zones correspond to wedge shaped openings 64 and 66. One or more characteristics of openings 64 and 66 such as dimensions, shape, and position within the aperture (and therefore position with respect to the system) may be adjustable such that the light scattered from the first and second sets of spots in one or more azimuthal collection zones is allowed to pass through the openings. The one or more characteristics of the openings may be adjusted in any manner known in the art. In addition, although aperture 60 is shown in FIG. 7 to include two openings through which scattered light is allowed to pass, it is to be understood that the aperture may include any number of openings (e.g., two or more openings) through which the scattered light passes.

The embodiment of aperture 60 shown in FIG. 7 is configured such that light scattered from the first and second sets of spots on the specimen at substantially all polar angles in the collection space of the system passes through openings 64 and 66. In other words, the light scattered in the azimuthal collection zones defined by openings 64 and 66 is not attenuated in the polar direction. However, the aperture may also be configured to block light in one or more selected polar collection zones in these openings.

Figure 8:
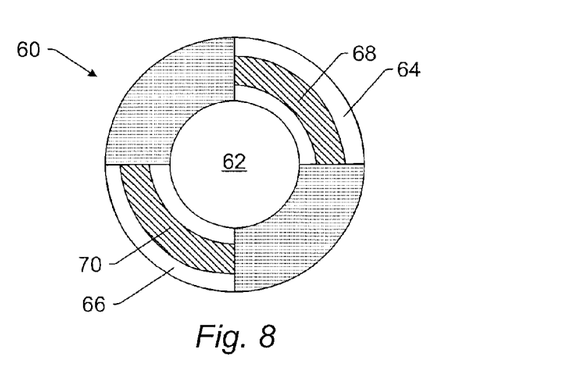

One such embodiment of aperture 60 is shown in FIG. 8. Aperture 60 shown in FIG. 8 may be configured as described above. In addition, as shown in FIG. 8, aperture 60 includes light blocking elements or portions 68 and 70 positioned in openings 64 and 66, respectively. Light blocking elements or portions 68 and 70 may have any suitable configuration known in the art. In this manner, aperture 60 may allow light scattered from the first and second sets of spots on the specimen at only a portion of the polar angles across the azimuthal collection zones defined by openings 64 and 66 to pass through the aperture and be detected. As such, when viewed at the plane of aperture 60 in FIG. 8, the polar collection zones correspond to radial zones in the aperture defined by the portions of openings 64 and 66 in which light blocking elements or portions 68 and 70 are not positioned. Although light blocking elements are shown in FIG. 8 positioned in each of the openings of the aperture, it is to be understood that such light blocking elements may be positioned in only some of the openings. In other words, in some of the azimuthal collection zones, the light may also be attenuated in the polar direction, while in other azimuthal collection zones, the light may not be attenuated in the polar direction.

In addition, light scattered at substantially all azimuthal angles in only one or more polar collection zones may be allowed to pass through the aperture and be detected by the system. In other words, the light scattered from the first and second sets of spots on the specimen may be attenuated in the polar direction, but not the azimuthal direction. For example, the aperture may be configured such that light scattered from the first and second spots on the specimen at all azimuthal angles in one or more polar collection zones is allowed to pass through the aperture, and the one or more polar collection zones may be selected using one or more light blocking elements or portions that may be configured as described above and may form one or more annular blocking "rings" in the aperture.

One or more characteristics of light blocking elements or portions 68 and 70 such as dimensions, shape, and position within the aperture (and therefore position with respect to the system) may be adjustable such that the light scattered from the first and second sets of spots in one or more polar and azimuthal collection zones is allowed to pass through the openings. The one or more characteristics of light blocking elements or portions 68 and 70 may be adjusted as described herein. Aperture 60 shown in FIGS. 6-8 may have any other suitable configuration known in the art.

The detection subsystem may also include one or more polarizing elements positioned in one or more of the openings in aperture 60 or any other spatial filter used in the embodiments described herein. For example, one or more polarizing elements may be positioned in the clear (unblocked) regions of the aperture or spatial filter. In another example, the clear (unblocked) regions of the aperture or spatial filter may be constructed out of one or more polarizing films or one or more other elements. In this manner, the polarization state of the scattered light reaching the detector(s) may be preferentially selected, which can enhance surface features and defects in some cases. Examples of apertures and polarizing components that may be included in the embodiments described herein are illustrated in commonly assigned, co-pending U.S. patent application Ser. No. 11/110,383 by Shortt et al. filed Apr. 20, 2005, which is incorporated by reference as if fully set forth herein. The embodiments described herein may be further configured as described in this patent application.

Aperture 60 may also be replaced with any other suitable optical element that can be used to independently select the one or more polar and/or azimuthal collection zones in which the light scattered from the first and second sets of spots is collected and detected. For example, aperture 60 can be replaced with one or more reflective optical elements positioned in the path of the scattered light collected by objective 17.

Figure 9:
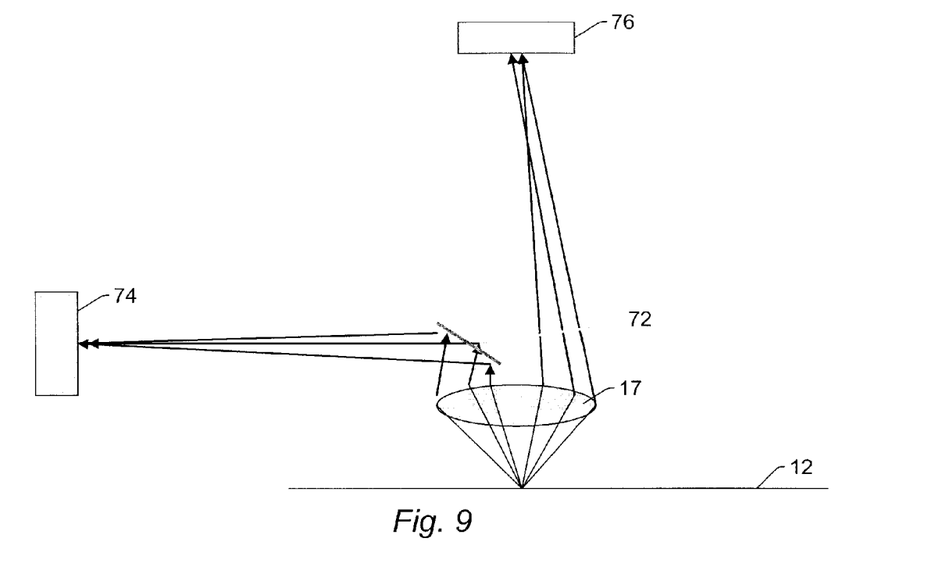
FIGS. 9-10 are schematic diagrams illustrating a side view of a portion of various embodiments of a system configured to determine a characteristic of a specimen by separately detecting light scattered from first and second sets of spots on a specimen in two or more azimuthal collection zones and/or two or more polar collection zones.

One such embodiment is illustrated in FIG. 9. This system is configured to direct multi-spot illumination scattered light in different azimuthal collection zones to different detection subsystems (e.g., different sets of detectors). For example, instead of using aperture 60 to block the light in various azimuthal collection zones, the system includes reflective optical element 72 (e.g., a mirror, a beam splitter, or any other suitable reflective optical element) positioned at the Fourier plane of objective 17. Unlike aperture 60, reflective optical element 72 is not configured to block a portion of the light scattered from the first and second sets of spots. Instead, reflective optical element 72 is configured to reflect a portion of the scattered light to another detection subsystem. In particular, reflective optical element 72 is configured to reflect a portion of the light scattered from the first and second sets of spots on the specimen to detection subsystem 74. Light scattered from the first and second sets of spots on the specimen that is not reflected by reflective optical element 72 is directed to detection subsystem 76. In this manner, reflective optical element 72 may be positioned at the Fourier plane of the system and may be configured to split the scattered light based on azimuthal (and/or polar) position. In addition, it is noted that although directing light to different detection subsystems based on azimuthal collection zones is preferably performed at the Fourier plane, directing light to different detection subsystems based on polar collection zones can be performed at any location along the collection path as described further herein.

Detection subsystems 74 and 76 may have any configuration described herein. For example, detection subsystem 74 may include two sets of detectors (one set for the obliquely illuminated spots, the other set for the normally illuminated spots) for detecting scatter at one set of azimuthal angles, and detection subsystem 76 may include two sets of detectors (one set for the obliquely illuminated spots, the other set for the normally illuminated spots) for detecting scatter at a different set of azimuthal angles. In this manner, light scattered in different azimuthal collection zones can be directed to different sets of detectors.

Although light scattered in two different azimuthal collection zones is separately detected by the system shown in FIG. 9, it is to be understood that the system may be configured to separately detect the light scattered from the first and second sets of spots on the specimen in any suitable number of azimuthal collection zones (e.g., two or more azimuthal collection zones). For example, the system shown in FIG. 9 may include more than one reflective optical element, which may be configured as described above with respect to reflective optical element 72, and which are positioned in the Fourier plane of the system at different azimuthal collection zones. Each of these reflective optical elements may be configured to direct the light to a different detection subsystem. The system shown in FIG. 9 may be further configured as described herein and has all of the advantages of other embodiments described herein.

The system may also or alternatively include one or more reflective optical elements configured and positioned to direct light in one or more different polar collection zones to different detection subsystems, different detectors, or different portions of a detector. For instance, the one or more reflective optical elements may include a mirror (e.g., a mirror having some curvature such as a circular mirror), a beam splitter, or any other suitable reflective optical element that is configured to direct light scattered in one or more different polar collection zones to different detection subsystems, different detectors, or different portions of a detector. In addition, one or more suitably configured apertures (which may be adjustable as described above) may be used in combination with the one or more reflective optical elements to allow only the light in the one or more polar collection zones to be detected and/or to alter the one or more polar collection zones. As such, the light scattered in one or more different polar collection zones may be separately and simultaneously detected.

Figure 10:
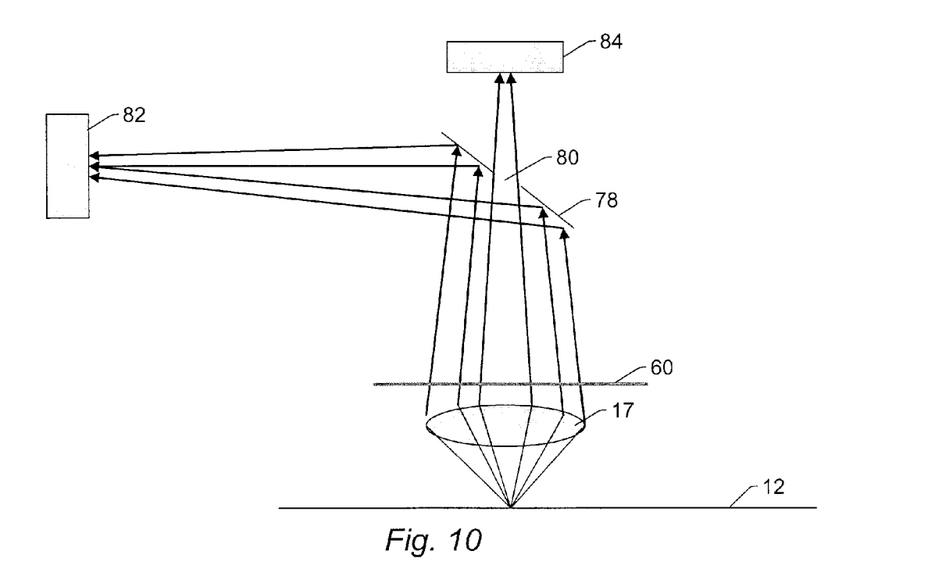

One such embodiment is illustrated in FIG. 10. In this system, separating light scattered in different polar collection zones may be performed using aperture(s) or reflective optical element(s) that are not positioned at the Fourier plane of the system (although the reflective optical element(s) described herein may be placed at the Fourier plane). Instead, the system may include a reflective optical element such as a mirror positioned at any location along the collection path configured to direct light in a selected polar collection zone to another detection subsystem. As shown in FIG. 10, the system may include aperture 60, which may be configured as described above. For example, aperture 60 may be configured as a spatial filter positioned at the Fourier plane of the system to block unwanted scattered light. The aperture may also block light in polar and/or azimuthal collection zones as described above. However, the system may also not include aperture 60.

The system also includes reflective optical element 78 positioned in the path of the light collected by objective 17. Reflective optical element 78 may include a beam splitter or a mirror having hole or opening 80 formed therethrough proximate to the center of the reflective optical element. Alternatively, the reflective optical element may have the inverse configuration. In addition, reflective optical element 78 does not have to be positioned at the Fourier plane of the system to separate light based on polar angles. Reflective optical element 78 is configured to direct light to detection subsystem 82. Light that is not reflected by reflective optical element 78 (e.g., light that passes through opening 80) is directed to detection subsystem 84. In this manner, reflective optical element 78 may be configured to split the scattered light based on polar position. In addition, it is noted that directing light to different detection subsystems based on polar collection zones can be performed at any location along the collection path.

Detection subsystems 82 and 84 may have any configuration described herein. For example, detection subsystem 82 may include two sets of detectors (one set for the obliquely illuminated spots, the other set for the normally illuminated spots) for detecting scatter at one set of polar angles (e.g., relatively large polar angles), and detection subsystem 76 may include two sets of detectors (one set for the obliquely illuminated spots, the other set for the normally illuminated spots) for detecting scatter at a different set of polar angles (e.g., relatively small polar angles). In this manner, light scattered in different polar collection zones can be separated towards different sets of detectors.

Although light scattered in two different polar collection zones is separately detected by the system shown in FIG. 10, it is to be understood that the system may be configured to separately detect the light scattered from the first and second sets of spots on the specimen in any suitable number of polar collection zones (e.g., two or more polar collection zones). For example, the system shown in FIG. 10 may include two or more reflective optical elements, which may be configured as described above with respect to reflective optical element 78, and which are positioned at different locations along the collection path. In one such example, the light collected by objective 17 may be directed to one reflective optical element, which is configured to reflect light at relatively large polar angles to a detection subsystem. Light that is not reflected by this reflective optical element may be directed to a second reflective optical element, which is configured to reflect light at smaller polar angles than the first reflective optical element. The light reflected by the second reflective optical element may be directed to a different detection subsystem, and the light that is not reflected by the second reflective optical element may be directed to another detection subsystem. In this manner, the system may include two (or more) reflective optical elements and three (or more) detection subsystems such that the light scattered from the first and second sets of spots on the specimen can be detected in three (or more) different polar collection zones. Each of these reflective optical elements and each of these detection subsystems may be further configured as described herein. The system shown in FIG. 10 may be further configured as described herein and has all of the advantages of other embodiments described herein.

It is noted that the figures are provided herein to generally illustrate various embodiments of a system configured to determine a characteristic of a specimen (e.g., to inspect a specimen). Obviously, the system configurations described herein may be altered to optimize the performance of the system as is normally performed when designing a commercial system. In addition, the systems described herein may be implemented using an existing inspection system (e.g., by altering the illumination subsystem configuration and/or detection subsystem configuration of an existing inspection system such as one of the SPx tools that are commercially available from KLA-Tencor, San Jose, Calif. to the configurations described herein). For some such systems, the functionality described herein may be provided as optional functionality of the system (e.g., in addition to other pre-existing functionality of the system). Alternatively, the systems described herein may be designed "from scratch" to provide a completely new system.

An additional embodiment relates to a method for determining a characteristic of a specimen. The method includes directing light to a first set of spots on the specimen at a normal angle of incidence while simultaneously directing light to a second set of spots on the specimen at an oblique angle of incidence. Directing the light to the first and second sets of spots may be performed as described herein. The method also includes detecting light scattered from the first and second sets of spots simultaneously to generate first output responsive to the light scattered from the first set of spots and second output responsive to the light scattered from the second set of spots. Detecting the light may be performed as described herein. The first and second outputs can be used to determine the characteristic of the specimen. Determining the characteristic of the specimen using the first and second outputs can be performed as described herein.

In one such embodiment, generating the first output includes generating different outputs, each of which corresponds to the light scattered from a different spot of the first set. In addition, generating the second output may include generating different outputs, each of which corresponds to the light scattered from a different spot of the second set. In this manner, if the characteristic of the specimen includes a presence of defects on the specimen, since each spot of the first and second sets may potentially illuminate a defect that none of the other spots illuminates, each of the different outputs of the first and second outputs corresponding to each of the different spots of the first and second sets may be used (e.g., monitored) to detect defects on the specimen.

In one embodiment, the method includes collecting the light scattered from the first and second sets of spots using a collector objective. Collecting the light may be performed as described herein. In another embodiment, detecting the light includes detecting the light scattered from the first and second sets of spots using a detector. Detecting the light in this manner may be performed as described herein. In a different embodiment, detecting the light includes detecting the light scattered from the first set of spots using a first detector (or first detectors) and detecting the light scattered from the second set of spots using a second detector (or second detectors). Detecting the light scattered from the first and second sets of spots using different detectors may be performed as described herein.

In some embodiments, detecting the light includes detecting the light scattered from the first and second sets of spots in one or more polar collection zones. In one such embodiment, the method includes independently selecting the one or more polar collection zones. The one or more polar collection zones may be selected as described herein.

In some embodiments, the light directed to the first set of spots and the light directed to the second set of spots has substantially the same wavelength. In another embodiment, the first and second sets of spots are arranged in two different rows of spots on the specimen. One embodiment of such an arrangement of the first and second spots is illustrated in FIG. 1. In one such embodiment, the two different rows are substantially parallel to each other. One embodiment of such an arrangement of the rows of spots is illustrated in FIG. 1. In an additional embodiment, the first and second sets of spots are spaced from each other on the specimen. An embodiment of such an arrangement of the first and second sets of spots is illustrated in FIG. 1. In a further embodiment, the first and second sets of spots are spaced from each other on the specimen to reduce cross talk between the first and second outputs.

In one embodiment, directing the light is performed such that the first and second sets of spots are directed to substantially the same area of the specimen per unit time. Directing the light in this manner may be performed as described further herein. In another embodiment, directing the light is performed such that the light can be directed to the first set of spots, the second set of spots, or the first and second sets of spots based on the characteristic of the specimen to be determined (e.g., the defects to be detected on the specimen). Directing the light in this manner may also be performed as described herein.

In some embodiments, the first and second sets of spots include the same number of spots. One embodiment of such first and second sets of spots is illustrated in FIG. 1. In a different embodiment, the first and second sets of spots include different numbers of spots. One embodiment of such first and second sets of spots is illustrated in FIG. 2. In a further embodiment, the second set of spots includes a larger number of spots than the first set. One embodiment of such first and second sets of spots is illustrated in FIG. 2.

Figure 3:
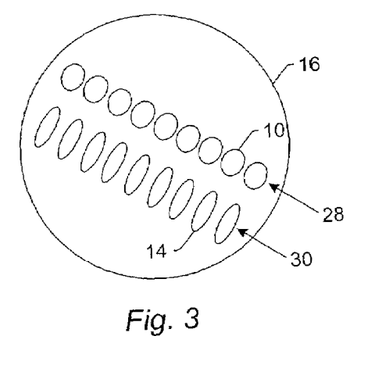

In one embodiment, the spots of the first and second sets have substantially the same aspect ratio. One embodiment of such spots is illustrated in FIG. 1. In another embodiment, the spots of the first and second sets have different aspect ratios. One embodiment of such spots is illustrated in FIG. 3. In some embodiments, the method includes selecting dimensions and aspect ratios of the spots of the first and second sets based on the characteristic of the specimen to be determined (e.g., the defects to be detected on the specimen).

In an embodiment, an intensity of the spots of the first set is substantially equal to an intensity of the spots of the second set. In a different embodiment, an intensity of the spots of the first set is different than an intensity of the spots of the second set. The intensity of the spots of the first and second sets may be altered and controlled as described herein. In addition, the intensity of the spots of the first and second sets may be selected as described herein. Each of the embodiments of the method described above may include any other step(s) described herein and has all of the advantages of other embodiments described herein.

A further embodiment relates to another method for determining a characteristic of a specimen. This method includes directing light to at least one spot on the specimen at a normal angle of incidence while simultaneously directing light to a set of spots on the specimen at an oblique angle of incidence. Alternatively, the method includes directing light to a set of spots on the specimen at a normal angle of incidence while simultaneously directing light to at least one spot on the specimen at an oblique angle of incidence. Such directing the light may be performed as described herein. The method also includes detecting light scattered from the at least one spot and the set of spots simultaneously to generate first output responsive to the light scattered from the at least one spot and second output responsive to the light scattered from the set of spots. Detecting the light can be performed as described herein. The first and second outputs can be used to determine the characteristic of the specimen. Determining the characteristic of the specimen using the first and second outputs can be performed as described herein.

Each of the embodiments of the methods described above may include any other step(s) described herein. In addition, each of the method embodiments described above may be performed as described herein. Moreover, each of the embodiments of the methods described above may be performed by one or more of the systems described herein. Furthermore, each of the embodiments of the methods described above has all of the advantages described herein.

Further modifications and alternative embodiments of various aspects of the invention may be apparent to those skilled in the art in view of this description. For example, systems and methods for determining a characteristic of a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to determine a characteristic of a specimen, comprising:
    an illumination subsystem configured to direct multiple beams of light simultaneously to a first set of spots on the specimen at a normal angle of incidence and to simultaneously direct multiple beams of light simultaneously to a second set of spots on the specimen at an oblique angle of incidence such that the first set comprises multiple simultaneously illuminated spots and the second set comprises multiple simultaneously illuminated spots; and
    a detection subsystem configured to detect light scattered from the first and second sets of spots simultaneously and to generate first output responsive to the light scattered from the first set of spots and second output responsive to the light scattered from the second set of spots, wherein the first and second outputs can be used to determine the characteristic of the specimen.

2. The system of claim 1, wherein the detection subsystem comprises a collector objective configured to collect the light scattered from the first and second sets of spots.

3. The system of claim 1, wherein the detection subsystem comprises a detector configured to detect the light scattered from the first and second sets of spots.

4. The system of claim 1, wherein the detection subsystem comprises a first detector configured to detect the light scattered from the first set of spots and a second detector configured to detect the light scattered from the second set of spots.

5. The system of claim 1, wherein the detection subsystem is further configured to detect the light scattered from the first and second sets of spots in one or more polar collection zones, and wherein the one or more polar collection zones are selected independently.

6. The system of claim 1, wherein the light directed to the first set of spots and the light directed to the second set of spots has substantially the same wavelength.

7. The system of claim 1, wherein the first and second sets of spots are arranged in two different rows of spots on the specimen.

8. The system of claim 1, wherein the first and second sets of spots are arranged in two different rows of spots on the specimen, and wherein the two different rows are substantially parallel to each other.

9. The system of claim 1, wherein the first and second sets of spots are spaced from each other on the specimen.

10. The system of claim 1, wherein the first and second sets of spots are spaced from each other on the specimen to reduce cross talk between the first and second outputs.

11. The system of claim 1, wherein the illumination subsystem is further configured such that the first and second sets of spots are directed to substantially the same area of the specimen per unit time.

12. The system of claim 1, wherein the illumination subsystem is further configured such that the light can be directed to the first set of spots, the second set of spots, or the first and second sets of spots based on the characteristic of the specimen to be determined.

13. The system of claim 1, wherein the first and second sets of spots further comprise the same number of spots.

14. The system of claim 1, wherein the first and second sets of spots further comprise different numbers of spots.

15. The system of claim 1, wherein the second set of spots further comprises a larger number of spots than the first set.

16. The system of claim 1, wherein the spots of the first and second sets have substantially the same aspect ratio.

17. The system of claim 1, wherein the spots of the first and second sets have different aspect ratios.

18. The system of claim 1, wherein dimensions and aspect ratios of the spots of the first and second sets are selected based on the characteristic of the specimen to be determined.

19. The system of claim 1, wherein an intensity of the spots of the first set is substantially equal to an intensity of the spots of the second set.

20. The system of claim 1, wherein an intensity of the spots of the first set is different than an intensity of the spots of the second set.

21. A method for determining a characteristic of a specimen, comprising:

directing multiple beams of light simultaneously to a first set of spots on the specimen at a normal angle of incidence using an illumination subsystem while simultaneously directing multiple beams of light simultaneously to a second set of spots on the specimen at an oblique angle of incidence using the illumination subsystem such that the first set comprises multiple simultaneously illuminated spots and the second set comprises multiple simultaneously illuminated spots; and detecting light scattered from the first and second sets of spots simultaneously to generate first output responsive to the light scattered from the first set of spots and second output responsive to the light scattered from the second set of spots, wherein the first and second outputs can be used to determine the characteristic of the specimen.

22. A system configured to determine a characteristic of a specimen, comprising:

an illumination subsystem configured to direct light to at least one spot on the specimen at a normal angle of incidence and to simultaneously direct multiple beams of light simultaneously to a set of spots on the specimen at an oblique angle of incidence such that the set of spots comprises multiple simultaneously illuminated spots; and a detection subsystem configured to detect light scattered from the at least one spot and the set of spots simultaneously and to generate first output responsive to the light scattered from the at least one spot and second output responsive to the light scattered from the set of spots, wherein the first and second outputs can be used to determine the characteristic of the specimen.

\* \* \* \* \*